Figure 1:
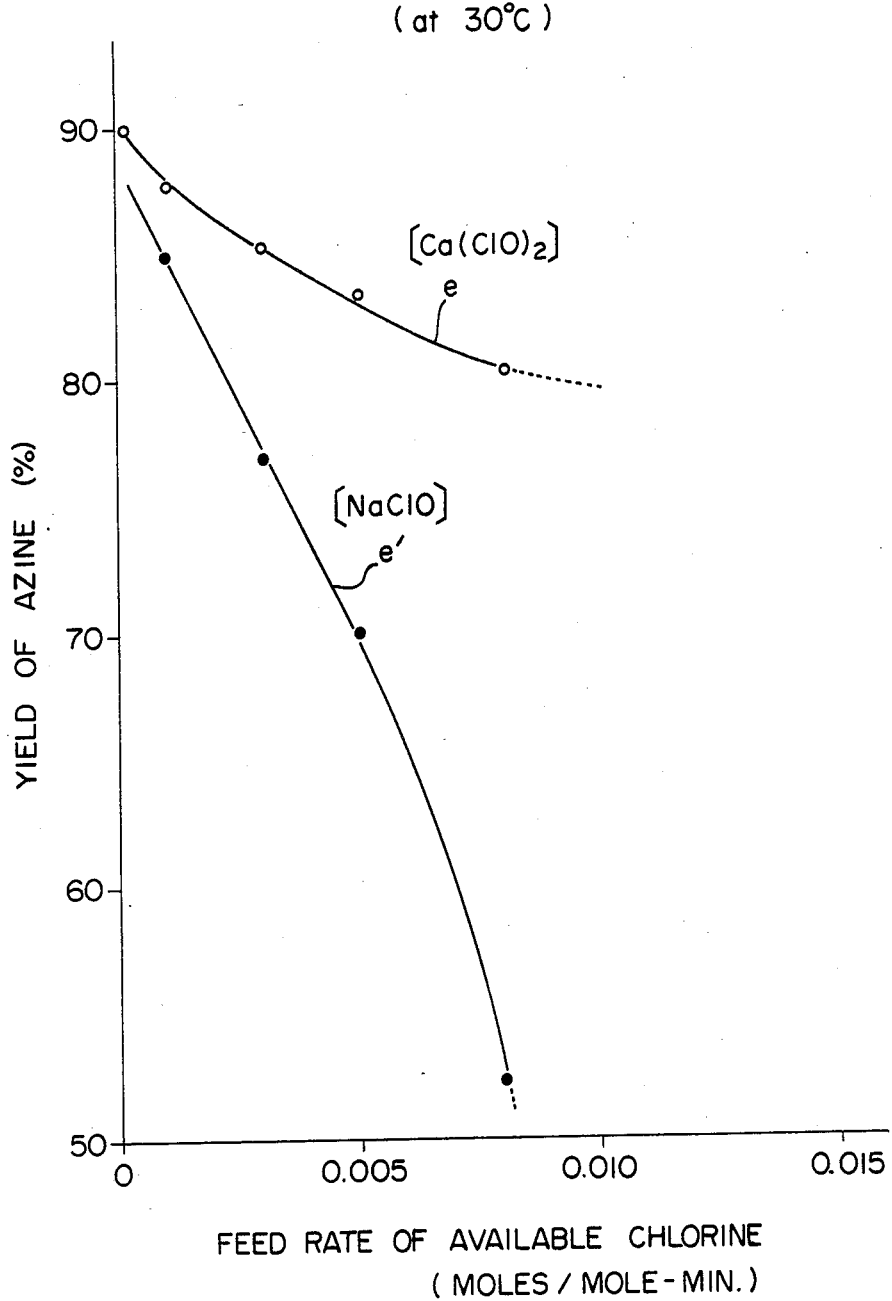
Figure 2:
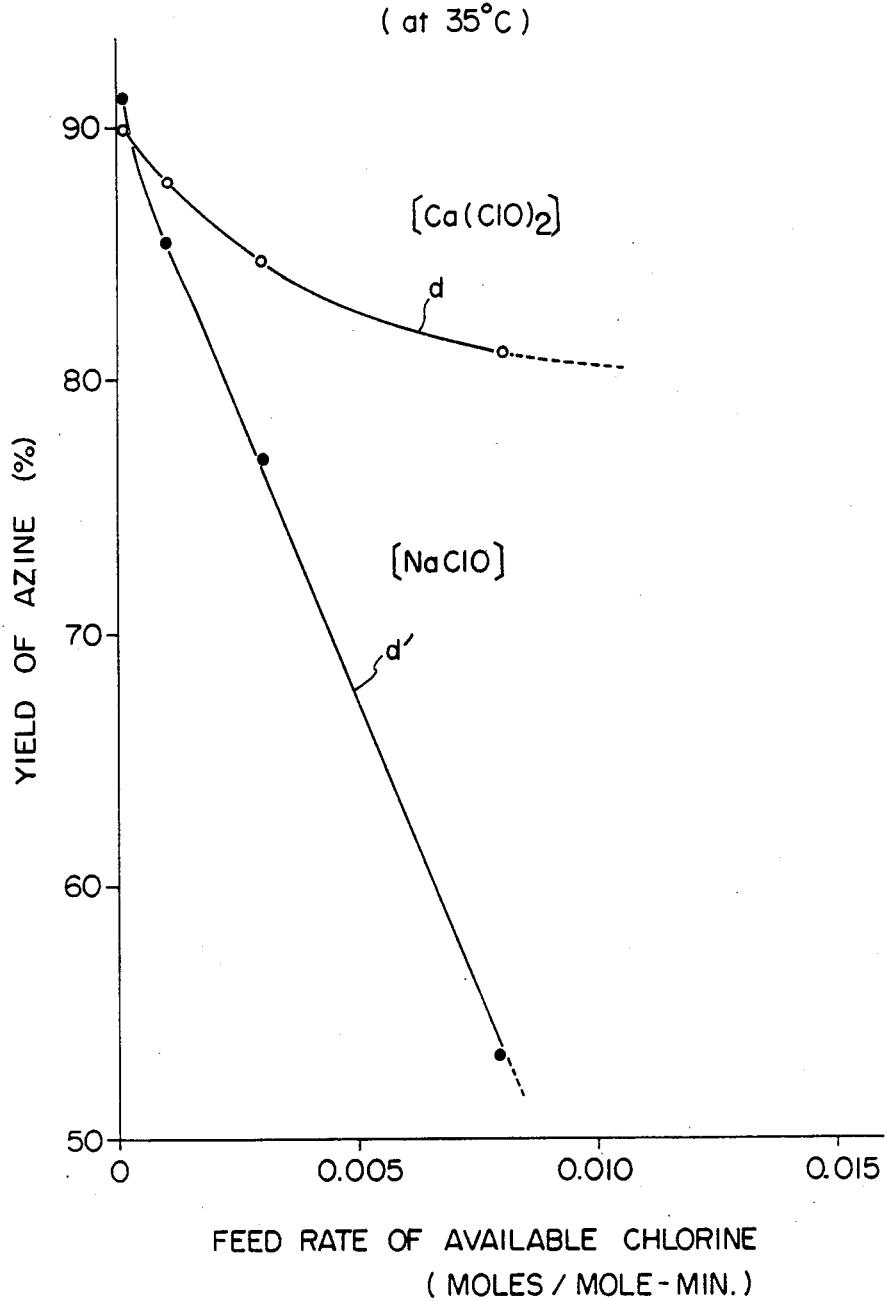
Figure 3:
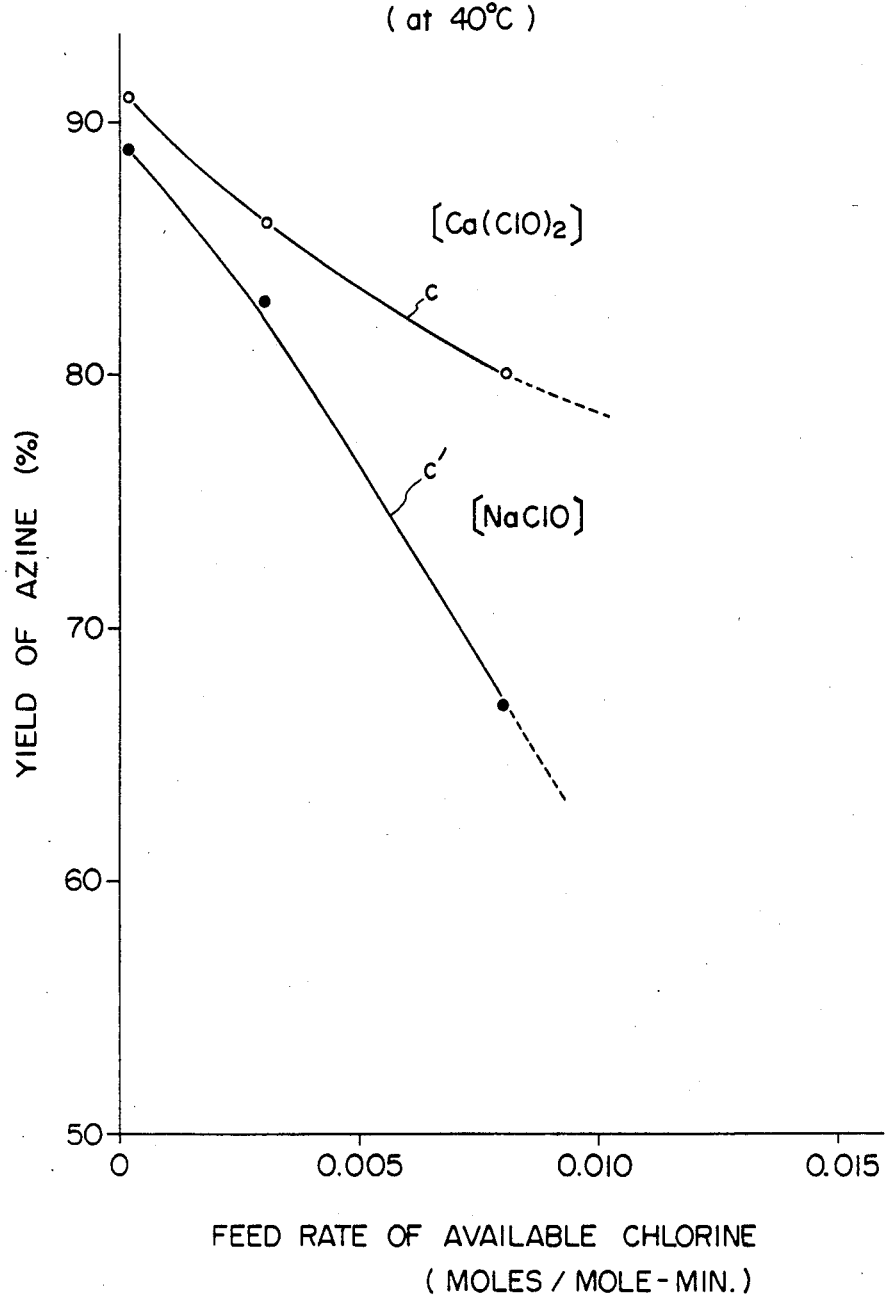
Figure 4:
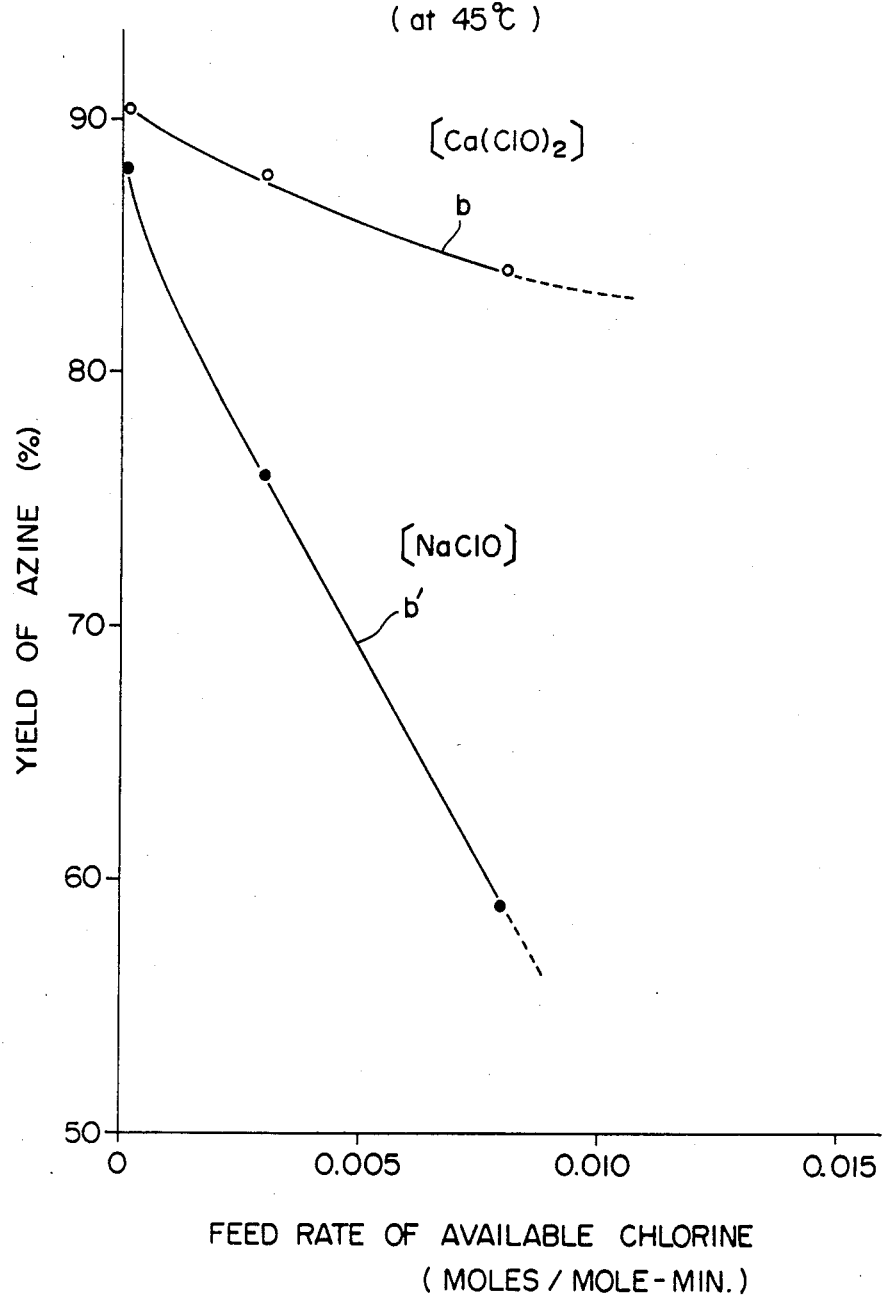
Figure 5:
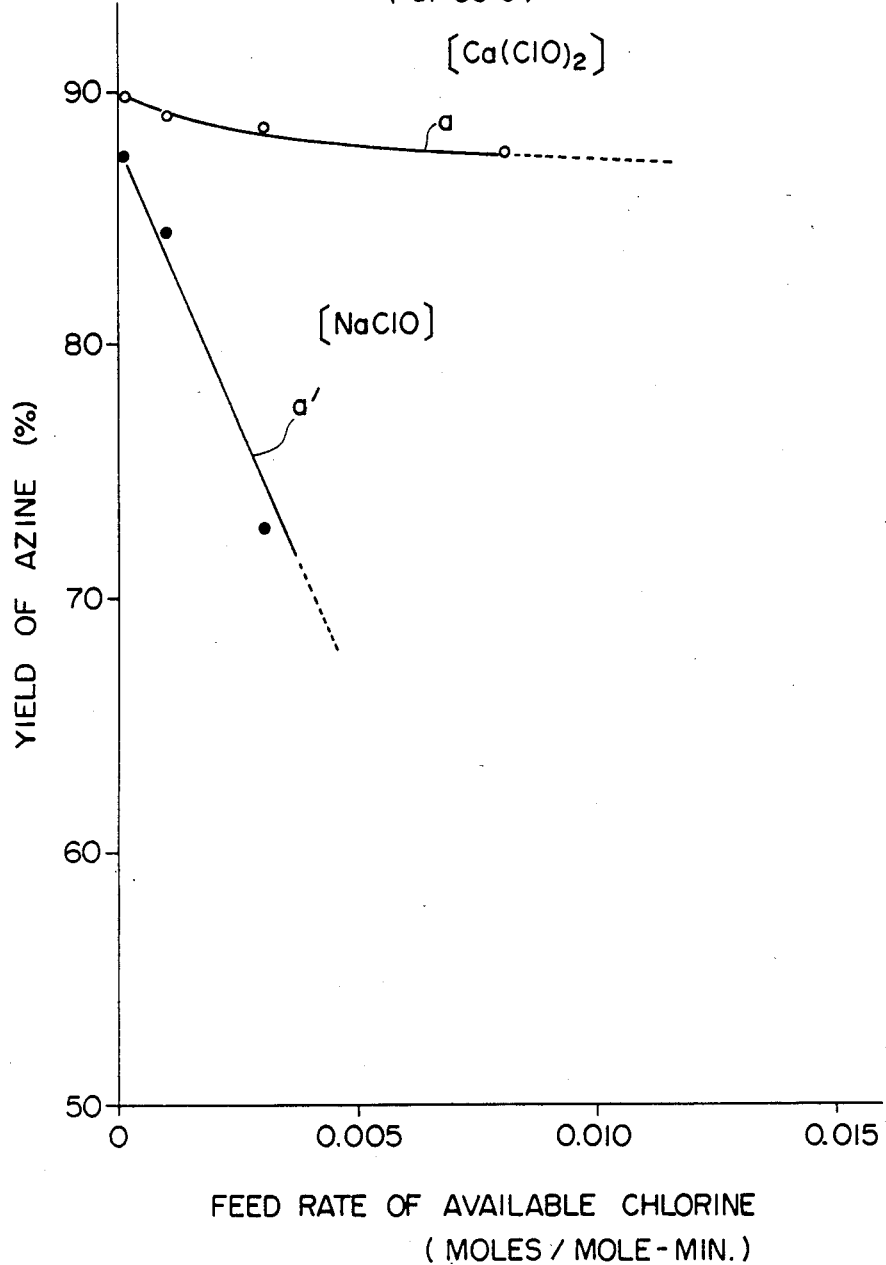

United States Patent [19]

Koshi et al.

[11] Patent Number: 4,647,697

[45] Date of Patent: Mar. 3, 1987

[54] PROCESS FOR PRODUCING AZINE COMPOUNDS

[75] Inventors: Minekazu Koshi, Namerikawa; Osamu Fukao, Tokyo; Taisuke Saito, Namerikawa; Tatsuo Sakan, Nagareyama; Seiichi Nakahara, Uozu, all of Japan

[73] Assignee: Nippon Carbide Kogyo Kabushiki Kaisha, Tokyo, Japan

[21] Appl. No.: 566,303

[22] Filed: Dec. 28, 1983

[30] Foreign Application Priority Data

Dec. 28, 1982 [JP] Japan ................. 57-227585

[51] Int. Cl.$^4$ ............................ C07C 119/00
[52] U.S. Cl. .................................... 564/249
[58] Field of Search ......................... 564/249

[56] References Cited

U.S. PATENT DOCUMENTS

| 3,382,041 | 5/1968 | Needham et al. | 564/249 |
| 3,728,390 | 4/1973 | Jenkins et al. | 564/249 |
| 3,875,231 | 4/1975 | Brandl et al. | 564/249 |
| 4,101,581 | 7/1978 | Needham et al. | 564/249 |

Primary Examiner—Natalie Trousof
Assistant Examiner—L. Hendriksen
Attorney, Agent, or Firm—Sherman and Shalloway

[57] ABSTRACT

In a process for producing an azine compound which comprises reacting ammonia with a hypochlorite in an aqueous medium in the presence of a carbonyl compound selected from the group consisting of acetone and methyl ethyl ketone at room temperature or a higher temperature and an atmospheric or higher pressure, the amounts of the carbonyl compound and ammonia being 2 to 5 moles and 5 to 35 moles, respectively, per mole of available chlorine of the hypochlorite; the improvement wherein (i) the reaction is carried out at a temperature of about 25° C. to about 60° C., (ii) the reaction is carried out by using calcium hypochlorite as the hypochlorite and while feeding an aqueous solution of calcium hypochlorite having an available chlorine concentration of 5 to 20% by weight to the reaction system, and (iii) the reaction is carried out while controlling the rate of feeding the aqueous solution of calcium hypochlorite to the reaction system such that the amount of available chlorine is 0.001 to 0.02 mole/mole-minute on an average per mole of ammonia and the carbonyl compound in the reaction system combined.

7 Claims, 6 Drawing Figures

PROCESS FOR PRODUCING AZINE COMPOUNDS

This invention relates to an improvement in a process for producing an azine compound useful, for example, as an intermediate for the production of hydrazine, which comprises reacting ammonia with a hypochlorite in an aqueous medium in the presence of a carbonyl compound selected from the group consisting of acetone and methyl ethyl ketone at room temperature or a higher temperature and an atmospheric or higher pressure.

While the prior art has exclusively used sodium hypochlorite, an alkali metal salt, as the hypochlorite, the present invention uses calcium hypochlorite, an alkaline earth metal salt, which is much cheaper. By performing the above reaction using calcium hypochlorite under a set of specified parameters or conditions in a smaller apparatus and with a shorter reaction time or residence time, the corresponding azine compound can be produced in a yield comparable to, or higher than, that attained by the prior art, and adverse effects on the yield of the product owing to temperature elevation can be reduced or avoided. The process of this invention, therefore, is suitable for industrial practice.

More specifically, this invention relates, in a process for producing an azine compound which comprises reacting ammonia with a hypochlorite in an aqueous medium in the presence of a carbonyl compound selected from the group consisting of acetone and methyl ethyl ketone at room temperature or a higher temperature and an atmospheric or higher pressure, the amounts of the carbonyl compound and ammonia being 2 to 5 moles and 5 to 35 moles, respectively, per mole of available chlorine of the hypochlorite, to the improvement wherein (i) the reaction is carried out at a temperature of about 25° C. to about 60° C., (ii) the reaction is carried out by using calcium hypochlorite as the hypochlorite and while feeding an aqueous solution of calcium hypochlorite having an available chlorine concentration of 5 to 20% by weight to the reaction system, and (iii) the reaction is carried out while controlling the rate of feeding the aqueous solution of calcium hypochlorite to the reaction system such that the amount of available chlorine is 0.001 to 0.02 mole/mole-minute on an average per mole of ammonia and the carbonyl compound in the reaction system combined.

The "Raschig method" is known for production of hydrazine. This method comprises reacting an aqueous solution of a hypochlorite, most commonly sodium hypochlorite, with ammonia to form chloramine ($NH_2Cl$) and then reacting it with an excessive amount of ammonia. But it has the defect that hydrazine cannot be obtained in a high yield because side reactions such as the reaction of the resulting chloramine with sodium hydroxide and the reaction of the chloramine with the hydrazine hydrate obtained are difficult to avoid.

A method for production of hydrazine which can remove this defect is also known. This method comprises reacting ammonia with a hypochlorite in the presence of a carbonyl compound in an aqueous medium at room temperature or higher temperature and an atmospheric or higher pressure to obtain a corresponding azine compound, for example dimethylketazine when acetone is used as the carbonyl compound or methylethylketazine when methyl ethyl ketone is used as the carbonyl compound, and hydrolyzing the resulting ketazine (this method will sometimes be referred to hereinafter as the "ketazine method"). It is generally known that in the production of an azine compound corresponding to the starting carbonyl compound, which is an intermediate in the "ketazine method", the carbonyl compound and ammonia are used in mole ratios partly overlapping those specified in the process of this invention (i.e., 2 to 5 moles of the carbonyl compound and 5 to 35 moles of ammonia per mole of available chlorine of the hypochlorite).

The present invention provides an improved process for producing azine compounds useful as intermediates in the aforesaid "ketazine method", particularly dimethylketazine and methylethylketazine from acetone and methyl ethyl ketone respectively.

The "ketazine method" and its improvements are known, for example, from Japanese Patent Publication No. 3552/1962 (published on June 6, 1962), Japanese Patent Publication No. 14971/1964 (published on July 29, 1964) and Japanese Laid-Open Patent Publication No. 10619/1972 (published on May 27, 1972; corresponding to west German Laid-Open Patent Publication No. 2,056,357 and U.S. Pat. No. 3,875,231).

Japanese Patent Publication No. 3552/1962 discloses a process for producing hydrazine from a hypochlorous acid solution and aqueous ammonia, characterized by reacting these compounds in the presence of a carbonyl compound of the formula

wherein $R_1$ represents an alkyl group or a hydrogen atom, $R_2$ represents an alkyl group, and $R_1$ and $R_2$ do not contain more than 5 carbon atoms in total.

Compounds including acetone and methyl ethyl ketone are cited therein as examples of the carbonyl compound. The above patent document states that the amount of the carbonyl compound used is preferably at least 2 moles per mole of hydrazine which may be obtained.

It describes that hydrazine is produced from a solution of sodium hypochlorite, an alkali metal hypochlorite, and aqueous ammonia by carrying out the reaction in the presence of the carbonyl compound, but does not touch upon the use of other hypochlorites. Naturally, it is totally silent on the use of calcium hypochlorite or any other alkaline earth metal hypochlorites. Furthermore, this document does not disclose anything about the combined set of conditions (i) to (iii) used in the process of this invention.

Japanese Patent Publication No. 14971/1964 (which is a patent of addition to the above-cited Japanese Patent Publication No. 3552/1962) discloses a process for producing hydrazine which comprises reacting a solution of sodium hypochlorite with an aqueous solution of ammonia in the presence of a carbonyl compound capable of forming with hydrazine a compound in the form of a hydrazone or azine, the amount of the carbonyl compound being at least 2 moles per mole of hydrazine which will be obtained, wherein the reaction components are mixed as intensely as possible and the reaction temperature is kept at not more than 40° C.

This Japanese patent document states that the above process is one embodiment of the process for producing hydrazine from a solution of sodium hypochlorite and an aqueous solution of ammonia in accordance with the first patent document cited above, and teaches that to achieve a good yield, the heat of reaction should be removed so that the temperature of the reaction system does not exceed 40° C. This second patent document as in the first one discloses only the use of sodium hypochlorite, and does not at all refer to the use of calcium hypochlorite or any other alkaline earth metal hypochlorites. It neither discloses the combined set of conditions (i) to (iii) used in the process of this invention.

U.S. Pat. No. 3,875,231 (corresponding to Japanese Laid-Open Patent Publication No. 10619/1972) discloses the recovery of reaction products of hydrazine and carbonyl compounds. The U.S. patent states that in the preparation of reaction products of hydrazine and carbonyl compounds, such as azines, by reacting ammonia with chlorine or a compound containing active chlorine, preferably bleaching lye, in an aqueous phase and in the presence of a carbonyl compound, the reaction products of hydrazine and carbonyl compounds are recovered by having present a hydrophilic substance in an amount sufficient to cause separation of the products into two phases, the lower of which is aqueous and the upper of which is organic and contains the hydrazine reaction products.

It states that as the hydrophilic substances which are not acids in reaction, electrolytes such as NaCl, KCl or CaCl$_2$ are particularly suitable as well as substances which are alkaline in reaction such as NaOH or NH$_3$. Example 6 of the U.S. patent uses chloride of lime containing active chlorine as the aforesaid active chlorine-containing compound. Example 8 of this patent (corresponding to Example 7 of the corresponding Japanese Laid-Open Patent Publication No. 10619/1972) describes bleaching lye (100 g per liter of active chlorine) as the active chlorine-containing compound.

In Example 6 of the U.S. patent, ammonia and chloride of lime are reacted in an aqueous medium in the presence of methyl ethyl ketone at a relatively low reaction temperature of 20° C. for 1 hour with stirring and then stirred further for 20 minutes. Of all working examples in the U.S. patent, Example 6 uses the highest calculable rate of feeding the active chlorine-containing compound, and the amount of available chlorine per mole of ammonia and the carbonyl compound in the reaction combined is only about 0.00082 mole/mole-minute for a reaction time of 1 hour, and about 0.00062 mole/mole-minute for a reaction time of 1 hour and 20 minutes. In Example 8 of the U.S. patent, the feed rate mentioned above, in terms of the amount of available chlorine, is about 0.00045 mole/mole-minute if ammonia added during the reaction is not considered, and about 0.00036 mole/mole-minute if such ammonia is considered. The U.S. patent proposes the recovery of reaction products of hydrazine and carbonyl compounds, and does not describe or suggest the technical problems encountered in the production of azine compounds by the "ketazine method" using calcium hypochlorite as the hypochlorite and guidelines for solving these problems. Naturally, it does not at all disclose the combined set of conditions (i) to (iii) specified in the present invention. On the contrary, the U.S. patent only discloses specific working examples whose conditions are quite inconsistent with the combined set of conditions used in the process of this invention.

As shown by the above-cited prior art references sodium hypochlorite has been used as an active chlorine-containing compound commonly and exclusively in industrial practice in the formation of an azine compound intermediate in the conventional "ketazine method". It was technical common knowledge as emphasized in the second patent document cited above that to obtain an azine compound in good yields, it is necessary to maintain the reaction temperature relatively low. The third patent document cited above showing the use of chloride of lime or bleaching lye gives a specific working example of the "ketazine method" in which a reaction temperature of 20° C. is used and the rate of feeding chloride of lime to the reaction is as low as 0.00082 mole/mole-minute at the highest.

The present inventors have made investigations in order to develop a process which can industrially advantageously produce an azine compound corresponding to a starting carbonyl compound, which is an intermediate compound in the "ketazine method", by using calcium hypochlorite which has never been used previously in industrial practice.

Consequently, they arrived at the new discovery that the "ketazine method" using calcium hypochlorite requires a combined set of conditions or parameters which are greatly different from conditions or parameters used in the conventional "ketazine method" using sodium hypochlorite. The investigations of the present inventors have shown that in the conventional "ketazine method" using sodium hypochlorite (to be sometimes referred to hereinafter simply as the conventional method), the yield of the azine compound increases when the rate of feeding an aqueous solution of sodium hypochlorite to the reaction system, in terms of the amount of available chlorine per mole of ammonia and the carbonyl compound in the reaction system combined, is small, and as the rate of feeding becomes higher, the yield of the azine compound tends to decrease abruptly. It has been found in accordance with this invention, however, that when calcium hypochlorite is used, it is necessary to satisfy the condition (iii) together with the other combined conditions; unexpectedly, better results are obtained at a higher feed rate, and at a feed rate above a certain point, the yield of the azine becomes higher by using the calcium salt than by using the sodium salt; and that variations in yield according to variations in feed rate are less than in the case of using the sodium salt, and the use of the calcium salt is advantageous for the allowance of feed rate control. The fact that a considerably lower feed rate than that specified in the condition (iii) of the process of this invention is employed in the third patent document cited above which gives an example of using chloride of lime or bleaching lye is presumably ascribable to the information obtained with regard to the sodium salt which those skilled in the art most would have naturally selected.

FIG. 1 shows variations in the yield of an azine in relation to the rate of feeding an aqueous solution of sodium hypochlorite to the reaction system, in terms of the amount of available chlorine (mole/mole-minute) per mole of ammonia and the carbonyl compound in the reaction system combined, in the conventional method, and variations in the yield of the azine in relation to the rate of feeding an aqueous solution of calcium hypochlorite in this invention under the same conditions at a reaction temperature of 30° C. FIGS. 2, 3, 4, and 5 show relations similar to FIG. 1 at a reaction temperature of 35°, 40°, 45°, and 50° C., respectively.

It is seen from lines a, b, c, d and e in these Figures that according to the process of this invention, even when the rate of feeding an aqueous solution of calcium hypochlorite to the reaction system is increased, the decrease of the yield of the final azine compound is relatively small, and that this tendency is observed over a relatively low temperature to a relatively high temperature, and the allowance with regard to variations in the reaction temperature is so wide that the process is industrially advantageous. It is seen by contrast that according to the conventional method, the yield of the final azine compound abruptly decreases with an increase in the rate of feeding an aqueous solution of sodium hypochlorite to the reaction system, and it is imperative to use a relatively low reaction temperature and a relatively low feed rate, as shown by lines a', b', c', d' and e' corresponding to the lines a, b, c, d and e.

The present inventors have also found that good results are obtained by satisfying the condition (ii) in combination with the other conditions. In Example 6 of the third patent document cited above showing the highest feed rate which, however, is much lower than the feed rate specified in the condition (iii) of the process of this invention, chloride of lime containing 27.7% of active chlorine is used. However, in the process of this invention carried out under the combined set of essential conditions (i) to (iii), the concentration of available chlorine in the aqueous solution of calcium hypochlorite to be fed into the reaction system is 5 to 20% by weight.

Figure 6:
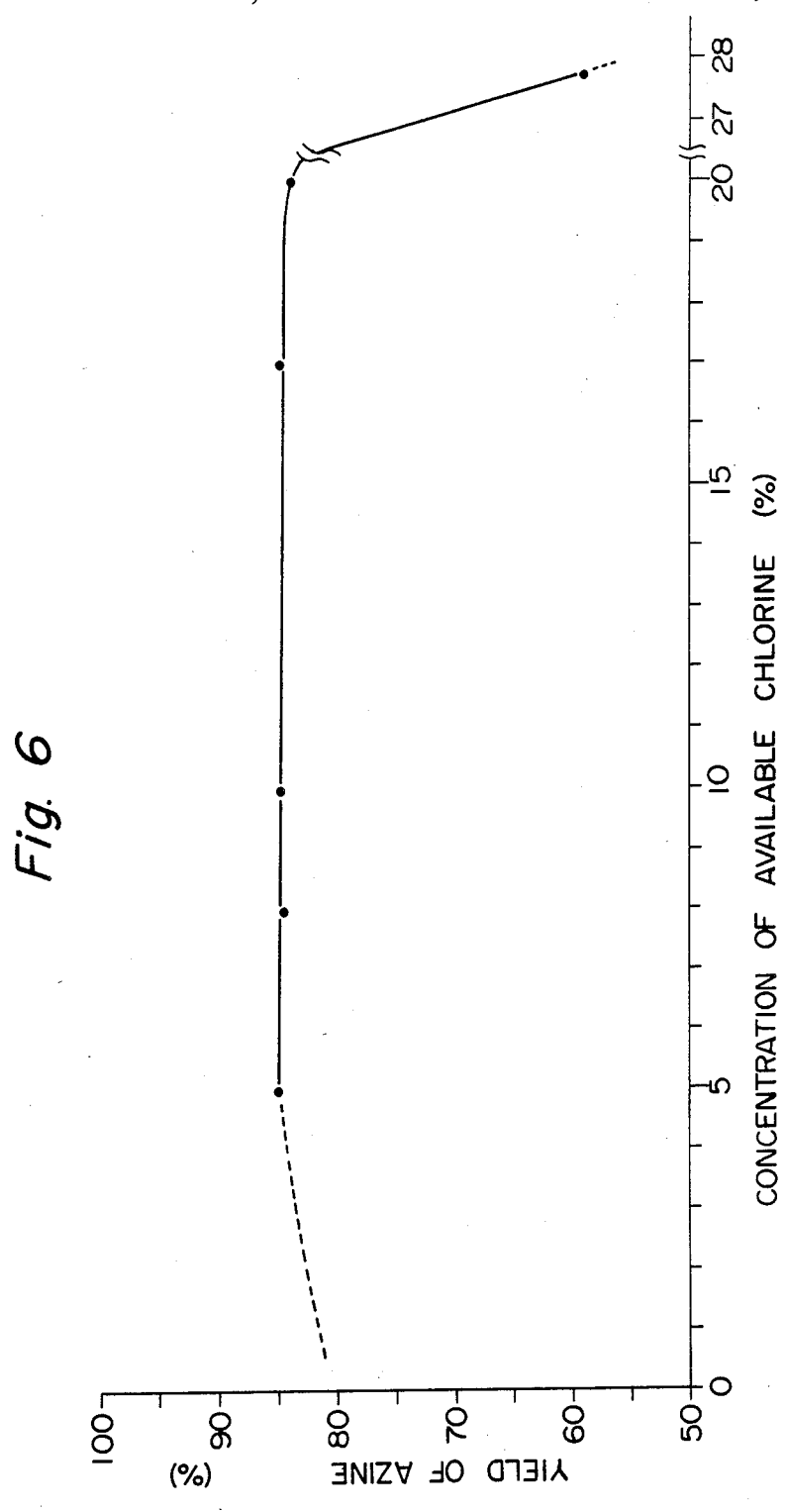

FIG. 6 shows an example of the relation between the concentration of available chlorine (ii) and the yield of azine (methyl ethyl ketazine) at a reaction temperature of 40° C. [condition (i)] and a feed rate of 0.003 mole/mole-minute [condition (iii)]. It is seen from FIG. 6 that under the combined set of conditions in accordance with this invention, a nearly constant yield of the final product can be achieved when the concentration of available chlorine is in the range of 5 to 20% by weight.

The present inventors have also found that the temperature set forth in condition (i) can be employed in combination with the other conditions. For example, the second patent document cited above teaches that the heat of reaction should be removed so as to control the temperature of the reaction system to not more than 40° C., and in Example 6 of the third patent document, which shows the highest feed rate, a reaction temperature of 20° C. is selected in using chloride of lime.

Investigations of the present inventors have led to the discovery that in the process of this invention using calcium hypochlorite unlike the conventional method, a temperature of about 25° to about 60° C. can be employed together with the other conditions, and this is advantageous for the allowance of temperature control, and that in spite of higher rates of feeding an aqueous solution of calcium hypochlorite to the reaction system than in the conventional method, the decrease of the yield of the azine compound with an increase in temperature can be much less than in the conventional method. This will be easily understandable from the foregoing description made with reference to FIGS. 1 to 5.

On the basis of the aforesaid new finding, the present inventors have found that the "ketazine method" using calcium hypochlorite requires the aforesaid combined set of parameters or conditions which are greatly different from the conventional method. Further investigations based on the new finding have now led to the discovery that an azine compound can be produced in a yield comparable to or higher than that attained by the conventional method in a smaller apparatus with a shorter reaction time or residence time than in the conventional method by a process for producing an azine compound, which comprises reacting ammonia with a hypochlorite in an aqueous medium in the presence of a carbonyl compound selected from the group consisting of acetone and methyl ethyl ketone at room temperature or a higher temperature and an atmospheric or higher pressure, the amounts of the carbonyl compound and ammonia being 2 to 5 moles and 5 to 35 moles, respectively, per mole of available chlorine of the hypochlorite, wherein (i) the reaction is carried out at a temperature of about 25° C. to about 60° C.,
(ii) the reaction is carried out by using calcium hypochlorite as the hypochlorite and while feeding an aqueous solution of calcium hypochlorite having an available chlorine concentration of 5 to 20% by weight to the reaction system, and
(iii) the reaction is carried out while controlling the rate of feeding the aqueous solution of calcium hypochlorite to the reaction system such that the amount of available chlorine is 0.001 to 0.02 mole/mole-minute on an average per mole of ammonia and the carbonyl compound in the reaction system combined.

Further advantages of the process of this invention are that calcium hypochlorite is much cheaper than the hypochlorites used in the conventional method, adverse effects on the yield of the azine by temperature elevation can be reduced or avoided, and the allowance of reaction control is wide.

It is an object of this invention to provide an improved industrially advantageous process for producing azine compounds in which calcium hypochlorite is used in accordance with the "ketazine method".

The above and other objects and advantages of this invention will become more apparent from the following description.

In practicing the process of this invention, ammonia and calcium hypochlorite are reacted in an aqueous medium in the presence of a carbonyl compound selected from the group consisting of acetone and methyl ethyl ketone under the combined conditions (i), (ii) and (iii). The reaction operation itself may be performed in accordance with known techniques except that the reaction is carried out under the conditions (i), (ii) and (iii). For example, an aqueous solution of calcium hypochlorite may be fed with stirring to an aqueous solution of ammonia and the carbonyl compound in the aqueous medium under the conditions (i), (ii) and (iii).

The reaction is carried out at room temperature or a higher temperature and an atmospheric or higher pressure by using 2 to 5 moles of the carbonyl compound and 5 to 35 moles of ammonia per mole of available chlorine of calcium hypochlorite.

In the process of this invention, a temperature of about 25° to about 60° C., preferably 30° to 58° C., more preferably 35° to 55° C., especially preferably 35° to 50° C., is used [condition (i)]. In the conventional method using sodium hypochlorite, the yield of the final azine compound abruptly decreases with an increase in temperature when the rate of feeding an aqueous solution of the hypochlorite to the reaction system increases. For example, the second patent document cited above teaches the use of temperatures of not more than 40° C., and the third patent document cited above which shows an example of reaction using calcium hypochlorite uses a reaction temperature of 20° C.

By contrast, the process of this invention is very advantageous for industrial practice both in regard to apparatus and operations because the decrease of the yield of the azine compound with an increase in temperature can be circumvented even when the reaction is carried out under the combined set of conditions (i) to (iii) at a higher rate of feeding to the reaction system in a smaller apparatus and with a shorter reaction time or residence time. According to the present invention, higher reaction temperatures can be used at a higher rate of feeding which is difficult to employ in the conventional method because of the consequent marked decrease in yield. Hence, the allowance of reaction temperature control is wider, and the process is advantageous over the conventional method. Since, however, the use of excessively low or high temperatures adversely affects the yield of the azine compound, suitable reaction temperatures should be selected within the above-specified range.

The reaction pressure may be an atmospheric or higher pressure, and, for example, pressures from atmospheric pressure to 5 atmospheres can be used.

In performing the process of this invention by feeding an aqueous solution of calcium hypochlorite to an aqueous solution of ammonia and the carbonyl compound, the latter may, of course, be a freshly prepared aqueous solution, but the mother liquor left after recovery of the azine compound from the reaction mixture can also be re-used. For example, an aqueous solution containing a part of the unrecovered azine compound, the unreacted carbonyl compound and ammonia obtained by working up the reaction mixture, for example recovering or removing the desired azine compound, the unreacted carbonyl compound and ammonia by extraction or distillation can be utilized. When the extracting operation is used in the work-up step, the residual mother liquor containing the extracting solvent dissolved therein may also be utilized. Accordingly, in the present invention, the aqueous solution of ammonia and the carbonyl compound also denotes such aqueous solutions to be re-used. The aqueous solution of calcium hypochlorite in the present invention denotes an aqueous solution or slurry of calcium hypochlorite containing impurities and by-products which may occur during the production of calcium hypochlorite.

In the process of this invention, the reaction is carried out while controlling the rate of feeding the aqueous solution of calcium hypochlorite such that the amount of available chlorine per mole of ammonia and the carbonyl compound in the reaction system combined is 0.001 to 0.02 mole/mole-minute, preferably 0.0015 to 0.01 mole/mole-minute, more preferably 0.002 to 0.008 mole/mole-minute, on an average [condition (iii)] under the combined set of conditions (i) to (iii).

As the rate of feeding becomes lower, it is necessary to increase the volume of the reactor or provide a number of reactors in order to obtain the azine compound in a certain specified yield per unit reaction time. This is unsuitable for industrial practice. When the volume of the reactor is increased, the power required for stirring the reaction system increases accordingly and the stirring efficiency becomes worse. As a result, calcium hypochlorite is difficult to diffuse uniformly in the reaction system, and the yield of the desired azine compound inevitably decreases. If an attempt is made to avoid the above troubles by increasing the number of reactors, the equipment and maintenance become more complex and expensive. On the other hand, the yield of the azine compound produced decreases if the rate of feeding becomes too high.

Accordingly, in the process of this invention, the reaction is carried out such that the rate of feeding the aqueous solution of calcium hypochlorite to the reaction system is as specified in condition (iii).

The feed rate in condition (iii) in this invention can be calculated as follows:

*When the reaction is carried out batchwise*

$$V_1 = \frac{X_1}{Y_1 + Z_1} \quad (1)$$

wherein $V_1$ is the rate of introducing available chlorine (moles/mole-minute), $X_1$ is the total amount of available chlorine introduced (moles/minute), $Y_1$ is the amount of ammonia charged (moles), and $Z_1$ is the amount of the carbonyl compound charged (moles).

*When the reaction is carried out continuously*

$$V_2 = \frac{X_2}{(Y_2 + Z_2)T} \quad (2)$$

wherein $V_2$ is the rate of introducing available chlorine (moles/mole-minute), $X_2$ is the total amount of available chlorine introduced (moles/minute), $Y_2$ is the amount of ammonia introduced (moles/minute), $Z_2$ is the amount of the carbonyl compound introduced (moles/minute), and $T$ is the residence time (minutes).

In the process of this invention, the feed rate of condition (iii) is selected so that under the combined set of conditions (i) to (iii), $V_1$ or $V_2$ satisfies the above equation.

$$0.001 \leq V_1 \text{ or } V_2 \leq 0.02$$

preferably $$0.0015 \leq V_1 \text{ or } V_2 \leq 0.01$$

more preferably $$0.002 \leq V_1 \text{ or } V_2 \leq 0.008$$

In the process of this invention, under the combined set of conditions (i) to (iii), the reaction is carried out by using calcium hypochlorite as the hypochlorite and while feeding an aqueous solution of calcium hypochlorite having an available chlorine concentration of 5 to 20% by weight, preferably 5 to 15% by weight, more preferably 5 to 12% by weight, to the reaction system [condition (ii)].

If the concentration of available chlorine becomes lower than the specified lower limit, the amount of the azine compound yielded per unit time decreases, and the concentration of the azine compound in the reaction mixture becomes too low. Consequently, an unduly large amount of energy is required in separating the azine compound after the reaction and recovering the unreacted carbonyl compound and ammonia, and the process becomes unsuitable for industrial practice. On the other hand, if the available chlorine concentration exceeds the specified upper limit, the aqueous solution of calcium hypochlorite has an excessively high concentration and lends itself to difficult handling. More-over, the yield of the desired azine compound is reduced. Hence, the available chlorine concentration should be properly selected within the abovespecified range.

In the process of this invention, it is also important that 2 to 5 moles, preferably 2 to 4 moles, more preferably 2.5 to 3.5 moles, of the carbonyl compound selected from acetone and methyl ethyl ketone and 5 to 35 moles, preferably 8 to 25 moles, more preferably 10 to 20 moles, of ammonia are used per mole of available chlorine of calcium hypochlorite. By employing the above mole ratios under the combined set of conditions (i), (ii) and (iii), it is possible to reduce effectively the energy required for separating the desired azine compound from the reaction mixture and recovering the unreacted ammonia and the unreacted carbonyl compound from it.

The process of this invention can be schematically shown below with regard to the production of dimethylketazine using acetone as the starting carbonyl compound.

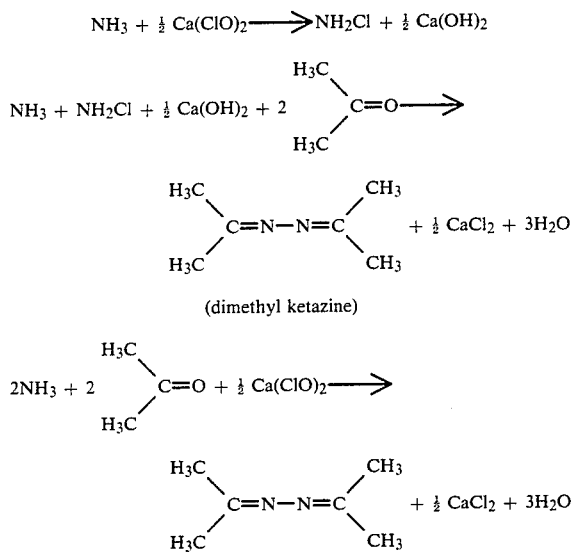

When methyl ethyl ketone is used as the starting carbonyl compound, methylethylketazine of the following formula can be obtained.

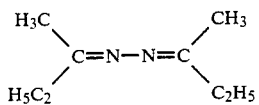

In the process of this invention, $CaCl_2$ is formed as a by-product in the reaction mixture instead of NaCl in the conventional method using sodium hypochlorite.

Preferably, under the combined set of conditions (i) to (iii) described above, the reaction in the process of this invention is carried out such that the concentration of by-product calcium chloride in the reaction mixture at the end of the reaction is 0.5 to 21% by weight, preferably 0.7 to 21% by weight, especially preferably 0.7 to 16% by weight [condition (iv)].

By controlling the concentration of the by-product calcium chloride in the reaction mixture at the end of the reaction to the above preferred range, the yield of the desired azine compound can be further increased. Means for controlling the concentration of the by-product calcium chloride to the above preferred range can be properly selected. For example, it can be controlled by properly selecting the reaction conditions experimentally. Or the control can be exercised by adding a suitable adjusting agent such as sodium hypochlorite and/or an alkali hydroxide such as sodium hydroxide to the reaction system. The time of addition to the reaction system can be properly selected and easily determined experimentally. For example, the concentration of by-product calcium chloride can be controlled by adding sodium hydroxide to the aqueous solution of ammonia and the carbonyl compound before and/or during the reaction.

After the reaction, the azine compound can be separated and recovered from the reaction mixture by extraction and/or distillation in accordance with procedures known in the practice of the "ketazine method".

Preferably, prior to the known extraction and/or distillation, the reaction mixture is subjected to an operation of removing solids composed mainly of by-product calcium hydroxide. This removing operation gives especially favorable results in industrial practice. According to this preferred embodiment, the reaction mixture is subjected to a solid removing operation by utilizing a suitable solid-liquid separating means. Complete removal of the solids is not necessary, and it is sufficient to reduce the solids content to about 110 ppm. For example, by reducing the solids content to about 20 to about 110 ppm, there will be removed various disadvantages in the extracting and/or distillation treatment, such as the adhesion of solids to the extracting and/or distilling device, blocking of the devices, the increase of water entrained in the extracting solvent layer, and hydrolysis of the azine during the distillation treatment owing to the increased amount of water. The solid removing operation thus gives especially favorable results in industrial practice. It can be effected, for example, by utilizing known solid-liquid separating means such as separating methods utilizing flocculation and precipitation, filtration under reduced pressure, filtration under elevated pressures, and centrifugation. Especially preferred from the standpoint of the efficiency of removing is a separating method using a filter having a leaf-shaped filter member.

The process of this invention can be carried out either batchwise or continuously, and for industrial practice, the continuous process is preferred.

In using a reactor for the continuous process, considerations should be given to sufficient diffusion and mixing of the materials within the reactor, and the reactor should be equipped with a device for controlling the heat of reaction.

The continuous process may be practiced by using a tubular reactor or a vessel reactor.

In the case of the tubular reactor, it is preferred to increase the linear speed so as to carry out the reaction uniformly in the reactor. For this purpose, the reactor preferably has a considerably large length for its diameter.

In the case of the vessel reactor, a stirring device or a pump stirring device is preferably used to perform the reaction uniformly therein.

In view of maintenance in the industrial practice, a continuous vessel-type reactor is preferred.

It has been found that when the continuous process is carried out under quite the same conditions as the conditions used for the batchwise process, the yield varies.

This variation has been found to be due to the fact that in the course of introducing an aqueous solution of calcium hypochlorite, the yield based on a trace of available chlorine introduced (to be referred to as the trace yield) varies with time. It has been found preferable to introduce the aqueous solution of calcium hypochlorite so that the following linear formula is established.

$$y = ax + b$$

wherein y is the trace yield (%) and x is the rate (%) of introducing available chlorine.

It has further been found that within the rate of introducing the aqueous solution of calcium hypochlorite in this invention, a and b are generally preferably $-0.38 \leq a \leq -0.02$ and $87.0 \leq b \leq 97.0$ especially preferably $-0.35 \leq a \leq -0.04$ and $88 \leq b \leq 96$.

For example, when the rate of introduction is 0.0036 mole/mole-minute and the reaction temperature is 40° C., $a = -0.143$ and $b = 93.0$.

In other words, when the process of this invention is carried out continuously, it is preferred to add the aqueous solution of calcium hypochlorite in portions from several places so that the above formula is satisfied while the specified average rate of introduction is maintained.

Furthermore, for industrial practice, it is preferred to carry out the process of this invention with a good production efficiency.

For example, the production efficiency ($K_f$) is defined as follows:

$$K_f = \frac{\left[\begin{array}{c}\text{Concentration of}\\ \text{the azine (wt. \%)}\end{array}\right] \times \left[\begin{array}{c}\text{Yield of the}\\ \text{azine (\%)}\end{array}\right]}{\left[\begin{array}{c}\text{Time required for the}\\ \text{reaction (minutes)}\end{array}\right]}$$

The process of the invention is carried out preferably such that $K_f \geq 8$, more preferably $K_f \geq 10$, especially preferably $K_f \geq 20$, above all $K_f \geq 30$.

The following examples illustrate the process of this invention more specifically. It should be understood that the invention is in no way restricted by these examples, and various changes and modifications are possible without departing from the scope of the invention as defined in the appended claims.

EXAMPLES 1 to 10 and COMPARATIVE EXAMPLES 1 to 10

A reaction vessel equipped with a stirrer and a thermometer was set in a constant-temperature vessel, and aqueous ammonia and each of the carbonyl compounds shown in Tables 1 to 4 were put in the reaction vessel. With stirring, an aqueous solution of the hypochlorite shown in Tables 1 to 4 was fed by means of a metering pump into the aqueous solution of ammonia and the carbonyl compound. The reaction was carried out under the conditions (i), (ii) and (iii) and the reactant mole ratios shown in these tables.

The conditions and results are shown in Tables 1-a and 1-b to 4-a and 4-b.

The data reported in Tables 1-a and 1-b directly demonstrates the importance of each of the requirements (i), (ii) and (iii). Thus, Example 1 and Comparative Examples 1 and 2 show the effect of reaction temperatures with all other parameters being the same. Comparing Example 1 with Comparative Examples 3 and 4 shows the effect of available Cl concentration (wt. %) (requirement (ii)). From Example 1 and Comparative Examples 5 and 6 the importance of the rate of feeding available Cl (mole/mole-min) (requirement (iii)) can be seen.

From the data reported in Tables 2-a, 2-b and Tables 3-a, 3-b, a direct side-by-side comparison can be made between the use of calcium hypochlorite according to the invention and sodium hypochlorite over a range of temperatures (35° C. and 50° C.) and feed rates (0.003 mole/mole-min and 0.008 mole/mole min). Thus Example 2 of Tables 2-a, 2-b corresponds to Comparative Example 7 of Tables 3-a, 3-b, the only variable being the type of hypochlorite; the available Cl concentration (ii), amount of hypochlorite, available Cl (moles), concentration and amount of aqueous ammonia, kind and amount of carbonyl compound, mole ratio of ammonia/carbonyl compound/available Cl, reaction temperature (i) and rate of feeding available Cl (iii) being the same. Similarly, in like manner, Example 3 corresponds to Comparative Example 8, Example 4 corresponds to Comparative Example 9, and Example 5 corresponds to Comparative Example 10.

The data in Tables 4-a and 4-b show the operability of the invention process over the scope of the variable parameters which constitute the invention process.

TABLE 1

| Run | Example 1 | Comparative Example 1 | 2 | 3 | 4 | 5 | 6 |
|---|---|---|---|---|---|---|---|
| Materials used | | | | | | | |
| Aqueous solution of calcium hypochlorite | | | | | | | |
| Available Cl concentration (wt. %) (ii) | 8 | " | " | 2 | 25 | 8 | " |
| Amount (g) | 887.5 | " | " | 3550 | 284 | 887.5 | " |
| Available Cl (moles) | 1 | " | " | " | " | " | " |
| Aqueous ammonia | | | | | | | |
| Concentration (wt. %) | 20 | " | " | " | " | " | " |
| Amount (g) | 1275 | " | " | " | " | " | " |
| Amount (moles) | 15 | " | " | " | " | " | " |
| Carbonyl compound | | | | | | | |
| Kind | MEK | " | " | " | " | " | " |
| Amount (g) | 216 | " | " | " | " | " | " |

TABLE 1-continued

| Run | Example 1 | Comparative Example 1 | 2 | 3 | 4 | 5 | 6 |
|---|---|---|---|---|---|---|---|
| Amount (moles) | 3 | " | " | " | " | " | " |
| Reaction conditions | | | | | | | |
| Mole ratio of ammonia/carbonyl compound/available chlorine | 15/3/1 | " | " | " | " | " | " |
| Temperature (°C.) (i) | 45 | 15 | 70 | 45 | " | " | " |
| Rate of feeding available Cl (moles/mole-min.) (iii) | 0.003 | " | " | " | " | 0.0006 | 0.05 |
| Results | | | | | | | |
| Azine concentration (wt. %) | 5.16 | 3.51 | 2.58 | 2.42 | 5.28 | 5.20 | 1.88 |
| Azine yield (%) | 87.6 | 59.6 | 43.8 | 87.1 | 66.9 | 88.3 | 31.9 |
| Time required for the reaction (min.) | 18.5 | 18.5 | 18.5 | 18.5 | 18.5 | 92.6 | 1 |
| Production efficiency ($K_f$) | 24.4 | 11.3 | 6.1 | 11.4 | 19.1 | 5.0 | 60.0 |
| Amount of hydrazine hydrate formed per unit time (V = 1,000) | 1 | 0.68 | 0.50 | 0.47 | 1 | 0.20 | 6.7 |
| Volume of the reaction vessel* | 1 | 1.5 | 2 | 2.1 | 1 | 5.0 | 0.15 |
| Concentration of calcium chloride after synthesis of the azine (wt. %) | 4.7 | 4.5 | 4.5 | 2.3 | 6.4 | 4.7 | 4.1 |

*The volume of the reaction vessel which was required to obtain the same amount of hydrazine hydrate per unit time.

TABLE 2

| Run | | Example 2 | 3 | 4 | 5 |
|---|---|---|---|---|---|
| Materials used | | | | | |
| Aqueous solution of calcium hypochlorite | Available Cl concentration (wt. %) (ii) | 8 | " | " | " |
| | Amount (g) | 887.5 | " | " | " |
| | Available Cl (moles) | 1 | " | " | " |
| Aqueous ammonia | Concentration (wt. %) | 20 | " | " | " |
| | Amount (g) | 1275 | " | " | " |
| | Amount (moles) | 15 | " | " | " |
| Carbonyl compound | Kind | MEK | " | " | " |
| | Amount (g) | 216 | " | " | " |
| | Amount (moles) | 3 | " | " | " |
| Reaction conditions | Mole ratio of ammonia/carbonyl compound/available chlorine | 15/3/1 | " | " | " |
| | Temperature (°C.) (i) | 35 | " | 50 | " |
| | Rate of feeding available Cl (moles/mole-min.) (iii) | 0.003 | 0.008 | 0.003 | 0.008 |
| Results | | | | | |
| Azine concentration (wt. %) | | 4.99 | 4.77 | 5.21 | 5.14 |
| Azine yield (%) | | 84.7 | 81.0 | 88.5 | 87.3 |
| Time required for the reaction (min.) | | 18.5 | 7 | 18.5 | 7 |
| Production efficiency ($K_f$) | | 22.8 | 55.2 | 24.9 | 64.1 |
| Amount of hydrazine hydrate formed per unit time (V = 1,000) | | 0.96 | 2.4 | 1 | 2.6 |
| Volume of the reaction vessel (*) | | 1 | 0.41 | 1 | 0.38 |
| Concentration of calcium chloride after synthesis of the azine (wt. %) | | 4.7 | 4.5 | 4.7 | 4.7 |

(*) The volume of the reaction vessel which was required to obtain the same amount of hydrazine hydrate per unit time.

TABLE 3

| Run | | Comparative Example 7 | 8 | 9 | 10 |
|---|---|---|---|---|---|
| Materials used | | | | | |
| Aqueous solution of sodium hypochlorite | Available Cl concentration (wt. %) (ii) | 8 | " | " | " |
| | Amount (g) | 887.5 | " | " | " |
| | Available Cl (moles) | 1 | " | " | " |
| Aqueous ammonia | Concentration (wt. %) | 20 | " | " | " |
| | Amount (g) | 1275 | " | " | " |
| | Amount (moles) | 15 | " | " | " |
| Carbonyl compound | Kind | MEK | " | " | " |
| | Amount (g) | 216 | " | " | " |
| | Amount (moles) | 3 | " | " | " |
| Reaction conditions | Mole ratio of ammonia/carbonyl compound/available chlorine | 15/3/1 | " | " | " |
| | Temperature (°C.) (i) | 35 | " | 50 | " |
| | Rate of feeding available Cl (moles/mole-min.) (iii) | 0.003 | 0.008 | 0.003 | 0.008 |
| Results | | | | | |
| Azine concentration (wt. %) | | 4.53 | 3.14 | 4.28 | 2.59 |
| Azine yield (%) | | 76.9 | 53.3 | 72.7 | 44.0 |
| Time required for the reaction (min.) | | 18.5 | 7 | 18.5 | 7 |
| Production efficiency ($K_f$) | | 18.8 | 23.9 | 16.8 | 16.3 |
| Amount of hydrazine hydrate formed per unit time (V = 1,000) | | 0.87 | 1.6 | 0.83 | 1.3 |
| Volume of the reaction vessel (*) | | 1.1 | 0.62 | 1.2 | 0.76 |
| Concentration of calcium chloride after synthesis of the azine (wt. %) | | — | — | — | — |

(*) The volume of the reaction vessel which was required to obtain the same amount of hydrazine hydrate per unit time.

TABLE 4

| Run | Example 6 | 7 | 8 | 9 | 10 |
|---|---|---|---|---|---|
| Materials used | | | | | |
| Aqueous solution of calcium hypochlorite | | | | | |
| Available Cl concentration (wt. %) (ii) | 7 | 10 | " | " | 8 |
| Amount (g) | 1014.3 | 710 | " | " | 887.5 |
| Available Cl (moles) | 1 | " | " | " | " |
| Aqueous ammonia | | | | | |
| Concentration (wt. %) | 20 | 25 | " | " | 20 |
| Amount (g) | 1700 | 1020 | 255 (ammonia) | 255 (ammonia) | 1275 (ammonia) |
| Amount (moles) | 20 | 15 | 255 (ammonia) | 255 (ammonia) | 1275 |
| Carbonyl compound | | | | | |
| Kind | MEK | 15 15 | 255 (ammonia) | ta 255 (ammonia) | Acetone |
| Amount (g) | 288 | 216 | 255 (ammonia) | 255 (ammonia) | 174 |
| Amount (moles) | 4 | 3 | 255 (ammonia) | 255 (ammonia) | 174 |
| Reaction conditions | | | | | |
| Mole ratio of ammonia/carbonyl compound/available chlorine | 20/4/1 | 15/3/1 | 255 (ammonia) | 255 (ammonia) | 174 |
| Temperature (°C.) (i) | 35 | 45 | 255 (ammonia) | 255 (ammonia) | 174 |
| Rate of feeding available Cl (moles/mole-min.) (iii) | 0.0026 | 0.003 | 255 (ammonia) | 255 (ammonia) | 174 |
| Results | | | | | |
| Azine concentration (wt. %) | 4.04 | 6.3 | 6.06 | 5.67 | 4.20 |
| Azine yield (%) | 86.7 | 87.6 | 84.3 | 78.9 | 87.7 |
| Time required for the reaction (min.) | 16 | 18.5 | 18.5 | 18.5 | 18.5 |
| Production efficiency ($K_f$) | 21.9 | 29.8 | 27.6 | 24.2 | 19.9 |
| Amount of hydrazine hydrate formed per unit time (V = 1,000) | 0.90 | 1.2 | 1.2 | 1.1 | 1 |
| Volume of the reaction vessel* | 1.1 | 0.82 | 0.82 | 0.91 | 1 |
| Concentration of calcium chloride after synthesis of the azine (wt. %) | 3.7 | 5.7 | 8.6 | 10.7 | 4.8 |

*The volume of the reaction vessel which was required to obtain the same amount of hydrazine hydrate per unit time.

EXAMPLE 11

Synthesis of azine

First, second and third reactors each having a capacity of 3 liters and equipped with a stirring device and a temperature adjusting device were connected in series for performance of a continuous reaction.

A 20% by weight aqueous solution of ammonia and methyl ethyl ketone were fed into the first reactor at a rate of 20.0 kg/hour (235.3 moles/hour) and 2.8 kg/hour (38.9 moles/hour), respectively. An aqueous solution of calcium hypochlorite having an available chlorine concentration of 10% by weight (11.1 kg/hour; 15.6 moles/hour) was divided into three equal portions which were introduced into the first, second and third reactors respectively. The reaction was thus carried out continuously at a temperature of 40° C. with a residence time of 15 minutes while maintaining the rate of feeding available chlorine at 0.0038 mole/mole-minute on an average. The mole ratio of ammonia/methyl ethyl ketone/available chlorine used in the reaction was 15/2.5/1.

The reaction mixture flowing from the outlet of the third reactor contained white fine particles which were clearly observed with the naked eye. It had a solids content of 315 ppm. The concentration of methylethyl ketazine analyzed was 5.39% by weight. The amount of the azine formed, which was calculated from its concentration, was 1,827 g/hour (azine yield 83.7%).

Separation of the solids

A closed filter comprising a SUS wire gauze (250 mesh; filtration area 678 cm²) as a filter member and granular perlite (Topco #34, a tradename for a product of Showa Chemical Industry Co., Ltd.) as a filtration aid were used. Perlite (68 g) was precoated on the wire gauze. Two filters (A and B) of the same type were set in parallel to the reactors for synthesis of the azine. Pipings and valves were provided so that the two filters could, independently from each other, permit pre-coating of the filtration aid, passing of the azine reaction mixture, and discharging of the cake.

Between the azine synthesizing reactors and the filters was disposed a device for introducing (body feeding) the filtration aid homogeneously into the azine reaction mixture.

Using the above apparatus, a 3% slurry of perlite was mixed at a rate of 0.57 kg/hour with the azine reaction mixture (33.9 kg/hour) flowing from the azine synthesizing reactor so that its body feed amount was about 500 ppm. The azine reaction mixture containing the perlite slurry was fed into the filter A by a pump. Initially, the filtration pressure was 0.2 kg/cm$^2$-G. When the filtration presure reached 4.0 kg/cm$^2$-G in 3.5 hours, the operation of the filter A was stopped, and the azine reaction mixture containing the perlite slurry was introduced into the filter B. During the operation of the filter B, the filter A was regenerated. The filtration operation was performed continuously by repeating this procedure. At the time of regeneration, the cake could be scraped off easily.

The filtrate which passed through the filter was so clear that no fine particles could be observed therein with the naked eye. The solids content of the filtrate at this time was 23 ppm.

Extraction of the azine

Three extraction-separators (A, B, C) each composed of a mixer equipped with a stirrer and having a net capacity of 0.83 liter and a settler having a separating area of 71 cm$^2$ were connected in series. The filtrate flowing from the filter was introduced into the mixer A at a rate of 34.4 kg/hour, and subjected continuously to countercurrent extraction using toluene as an extraction solvent in the mixer C in an amount corresponding to 20% of the azine reaction mixture (i.e., 6.8 kg/hour).

Analysis of the toluene layer flowing from the settler A showed that it contained methylethylketazine in a concentration of 19.2% by weight. The amount of the azine extractted, calculated from its concentration, was 1,803 g/hr. The ratio of extraction of the azine from the reaction mixture was 98.7%. The toluene layer contained 0.35% by weight of water.

After the lapse of more than 72 hours from the starting of the operation, scarcely any formation of a scum-like material in the extractors was observed, and the apparatus did not show any reduction in ability.

What is claimed is:
1. In a process for producing an azine compound which comprises reacting ammonia with a hypochlorite in an aqueous medium in the presence of a carbonyl compound selected from the group consisting of acetone and methyl ethyl ketone at room temperature or a higher temperature and an atmospheric or higher pressure, the amounts of the carbonyl compound and ammonia being 2 to 5 moles and 5 to 35 moles, respectively, per mole of available chlorine of the hypochlorite; the improvement wherein
 (i) the reaction is carried out at a temperature of about 25° C. to about 60° C.,
 (ii) the reaction is carried out by using calcium hypochlorite as the hypochlorite and while feeding an aqueous solution of calcium hypochlorite having an available chlorine concentration of 5 to 20% by weight to the reaction system, and
 (iii) the reaction is carried out while controlling the rate of feeding the aqueous solution of calcium hypochlorite to the reaction system such that the amount of available chlorine is 0.001 to 0.02 mole/mole-minute on an average per mole of ammonia and the carbonyl compound in the reaction system combined.

2. The process of claim 1 wherein the temperature in (i) is 30° to 58° C.

3. The process of claim 1 wherein the available chlorine concentration in (ii) is 5 to 15% by weight.

4. The process of claim 1 wherein the amount of available chlorine in (iii) is 0.0015 to 0.01 mole/mole-minute on an average.

5. The process of claim 1 which further comprises the improvement wherein (iv) the reaction is carried out so that the concentration of by-product calcium chloride in the reaction mixture at the end of the reaction is 0.5 to 21% by weight.

6. The process of claim 2 wherein the available chlorine concentration in (ii) is 5 to 15% by weight and the amount of available chlorine in (iii) is 0.0015 to 0.01 mole/mole-minute on an average.

7. The process of claim 6 which further comprises the improvement wherein (iv) the reaction is carried out so that the concentration of by-product calcium chloride in the reaction mixture at the end of the reaction is 0.5 to 21% by weight.

* * * * *